United States Patent
Hirayama

[11] Patent Number: 6,092,032
[45] Date of Patent: Jul. 18, 2000

[54] ELECTROCONDUCTIVE ROLLER AND APPARATUS AND METHOD FOR TESTING IT

[75] Inventor: Naka Hirayama, Tokyo, Japan

[73] Assignee: Nitto Kogyo Co., Ltd., Tokyo, Japan

[21] Appl. No.: 09/293,309

[22] Filed: Apr. 16, 1999

Related U.S. Application Data

[62] Division of application No. 09/036,157, Mar. 6, 1998.

[30] Foreign Application Priority Data

Mar. 12, 1997 [JP] Japan ................................. 9-074652
Jun. 12, 1997 [JP] Japan ................................. 9-074651

[51] Int. Cl.⁷ .................................................. G01N 21/57
[52] U.S. Cl. ................................ 702/115; 702/40; 492/9
[58] Field of Search .................... 702/40, 115; 492/9, 492/10, 11; 250/559.16; 427/494; 356/446, 445

[56] References Cited

U.S. PATENT DOCUMENTS

| | | | |
|---|---|---|---|
| 3,999,864 | 12/1976 | Mutter | 356/212 |
| 5,155,530 | 10/1992 | Larson et al. | 355/208 |
| 5,365,313 | 11/1994 | Nagamochi et al. | 355/208 |
| 5,401,977 | 3/1995 | Schwarz | 250/559 |
| 5,552,890 | 9/1996 | Nanna et al. | 356/369 |
| 5,748,221 | 5/1998 | Castelli et al. | 347/232 |
| 5,925,889 | 7/1999 | Guillory et al. | 250/559.16 |
| 5,991,017 | 11/1999 | Clark | 356/237 |
| 6,018,396 | 1/2000 | Rapaport et al. | 356/446 |
| 6,031,620 | 2/2000 | Typpo | 356/445 |

*Primary Examiner*—Patrick Assouad
*Attorney, Agent, or Firm*—Pitney, Hardin Kipp and Szuch LLP

[57] ABSTRACT

An electroconductive roller which is to be installed in an image forming apparatus is provided with a core, a roller body which includes an elastic member having conductivity, and is provided on the outer circumference of said core, and an electroconductive coating layer covering an outer circumferential surface of said roller body. When glossiness of said coating layer is measured, a difference between common logarithms of a maximum value and a minimum value of measurement values is less than 0.1.

13 Claims, 2 Drawing Sheets

ELECTROCONDUCTIVE ROLLER AND APPARATUS AND METHOD FOR TESTING IT

This application is a divisional application of U.S. patent application Ser. No. 09/036,157 filed Mar. 6, 1998.

BACKGROUND OF THE INVENTION AND RELATED ART STATEMENT

The present invention relates to an electroconductive roller provided in a device used as a process equipment in an image forming apparatus and testing method and testing device for testing the surface condition of the electroconductive roller used in the image forming apparatus, and more particularly, to testing method and testing device for testing the surface condition of the electroconductive roller which influences the quality of an image formed by the image forming apparatus.

Conventionally, as a device used as a process equipment in an image forming apparatus such as an electronic copying machine or a laser-beam printer, a developing device which supplies toner onto a photosensitive drum so as to develop (visualize) an electrostatic latent image formed on the photosensitive drum is known. In recent years, some image forming apparatuses, which use non-magnetic single-component toner, employ a developing roller such as an electroconductive roller as a part in the developing device to transfer the toner.

The developing roller is formed by, e.g., providing a roller body of electroconductive rubber on the outer periphery of a metal core, and coating the outer peripheral surface of the roller body with electroconductive resin. In this construction, the toner is charged and adsorbed by the friction between the outer peripheral surface and the toner, and the toner is transferred onto the outer peripheral surface of the photosensitive drum via fine irregularities of the outer peripheral surface of the developing roller, by rotation of the developing roller.

In the conventional art, the surface roughness (including so-called "waviness") of the developing roller has been widely noticed as a factor to influence the quality of an image formed by the image forming apparatus. The quality of the developing roller has been managed based on how to maintain the surface roughness within a predetermined range; in other words, the quality management has been made such that the developing roller having surface roughness out of the predetermined range is discarded as a bad (no good) product.

In this manner, to test the surface roughness of the developing roller, based on the Japanese Industrial Standard (JIS), a testing needle must be brought into contact with the outer peripheral surface of the developing roller, which might damage the peripheral surface. In this testing, even if the test result is "good", a developing roller with a damaged surface must be discarded as a defective product.

Further, the surface roughness test takes a very long time. In a case where the moving speed of the testing needle is set to 0.3 mm/sec and the outer peripheral surface of the developing roller is $\phi$16 mm, if the test is performed on the entire outer peripheral surface of the developing roller, the testing length is about 50.24 mm, and it takes about 3 minutes to complete this test. In practice, it is impossible to test all the developing rollers from the viewpoint of productivity, and improvement of this testing method is required.

On the other hand, to avoid damaging the outer peripheral surface of a developing roller, the developing roller is installed in an image forming apparatus without the above surface roughness test, and an image of "solid black", for example, is formed on a sheet by actually performing image forming process of the apparatus, and the density unevenness of the image is judged (so-called image test by actually using image forming apparatus). However, in this test, if it is determined that the image quality is degraded due to a bad developing roller, the developing roller must be replaced with a new developing roller, and thereafter, the same test must be performed on the apparatus again. In this manner, the efficiency of this test is very low and it must be improved.

SUMMARY OF THE INVENTION

The present invention has been made in consideration of the above situation, and has its primary object to provide an electroconductive roller for an image forming apparatus, which maintains excellent quality of an image formed by the image forming apparatus.

Further object of the present invention is to provide an electroconductive roller for an image forming apparatus, which enables a test of surface roughness of a developing roller which influences the quality of an image formed by the image forming apparatus, before the developing roller is installed in the image forming apparatus and the image test is performed.

Further, a different object of the present invention is to provide an electroconductive roller for an image forming apparatus, which enables the test of the surface roughness of a developing roller which influences the quality of an image formed by the image forming apparatus, by a predetermined amount.

Further, another object of the present invention is to provide an electroconductive roller for an image forming apparatus, which enables the test of the surface roughness of a developing roller which influences the quality of an image formed by the image forming apparatus, in non-contact status.

Further, a still further object of the present invention is to provide testing method and apparatus for an electroconductive roller for an image forming apparatus, which test the surface condition of the electroconductive roller which influences the quality of an image formed by the image forming apparatus, before the electroconductive roller is installed in the image forming apparatus and the image test is performed.

Further, a still another object of the present invention is to provide a testing method and apparatus for an electroconductive roller for an image forming apparatus, which test the surface condition of the electroconductive roller which influences the quality of an image formed by the image forming apparatus, in measurement by a predetermined amount.

Further, a still different object of the present invention is to provide testing method and apparatus for an electroconductive roller for an image forming apparatus, which test the surface condition of the electroconductive roller which influences the quality of an image formed by the image forming apparatus, in non-contact status.

In order to attain the above-mentioned objects, there is provided a electroconductive roller according to a first aspect of the present invention which is to be installed in an image forming apparatus, and characterized in that, when glossiness of an outer circumferential surface of said roller is measured, a difference between common logarithms of a maximum value and a minimum value of measurement values is less than 0.1.

According to a second aspect of the present invention, there is provided an electroconductive roller which is to be installed in an image forming apparatus, comprising a core; a roller body including an elastic member having conductivity, provided on the outer circumference of said core; and an electroconductive coating layer covering an outer circumferential surface of said roller body, wherein when glossiness of said coating layer is measured, a difference between common logarithms or a maximum value and a minimum value of measurement values is less than 0.1

According to a third aspect of the present invention, there is provided an electroconductive roller which is to be installed in an image forming apparatus, characterized in that, when glossiness of an outer circumferential surface of said roller is measured, a ratio of a difference between a maximum value and a minimum value of measurement values with respect to an average value of the measurement values is less than 20%.

According to a fourth aspect of the present invention, there is provided an electroconductive roller which is to be installed in an image forming apparatus, comprising: a core; a roller body including an elastic member having conductivity, provided on the outer circumference of said core; and an electroconductive coating layer covering an outer circumferential surface of said roller body, wherein when glossiness of said coating layer is measured, a ratio of a difference between a maximum value and a minimum value of measurement values with respect to an average value of the measurement values is less than 20%.

According to a fifth aspect of the present invention, there is provided a method for testing an electroconductive roller which is to be installed in an image forming apparatus, comprising steps of: a first step of setting a formed electroconductive roller at a position where a glossimeter can perform measurement on said electroconductive roller; a second step of measuring glossiness of an outer circumferential surface of said electroconductive roller using said glossimeter; a third step of performing a predetermined calculation on glossiness information of the outer circumferential surface of said electroconductive roller measured by said glossimeter; and a fourth step of comparing the result of said calculation with a predetermined threshold value and judging surface condition of said electroconductive roller.

According to a sixth aspect of the present invention, there is provided an apparatus for testing an electroconductive roller which is to be installed in an image forming apparatus, comprising placement means for placing a formed electroconductive roller, rotatably; rotation means for rotate-driving said electroconductive roller placed on said placement means, on a central axis of said electroconductive roller; measurement means for measuring glossiness of an outer circumferential surface of said electroconductive roller rotate-driven by said rotation means; calculation means for performing a predetermined calculation on glossiness information obtained by said measurement means; and judgment means for comparing the result of the calculation with a predetermined threshold value and judging surface condition of said electroconductive roller.

BRIEF DESCRIPTION OF THE DRAWINGS

These and other objects of the subject invention will become more fully apparent as the following description is read in light of the attached drawings wherein.

DETAILED DESCRIPTION OF THE PREFERRED EMBODIMENT

A preferred embodiment of the present invention will now be described in detail in accordance with the accompanying drawings.

[Developing Roller 10]

In the following embodiment, a developing roller 10 will be described as an electroconductive roller used in an image forming apparatus such as an electronic copying machine, a laser-beam printer or an electronic facsimile device. The developing roller 10 is used as a toner supplying (transfer) member in a developing device to supply (feed) toner (in this embodiment, non-magnetic single-component toner) onto the outer circumferential surface of a photosensitive body (specifically, photosensitive drum) as an image carrier, and visualize (i.e., develop) an electrostatic latent image formed on the outer circumferential surface of the photosensitive body.

Figure 1:
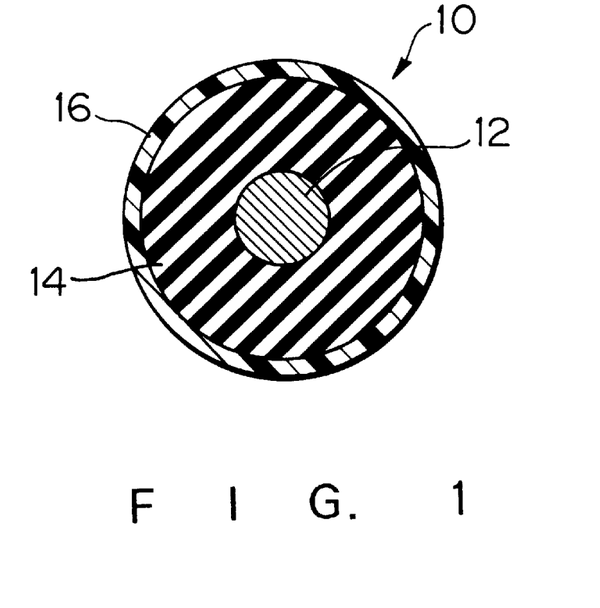
FIG. 1 is a side view showing a construction of a developing roller as an electroconductive roller according to one embodiment of the present invention.

As shown in FIG. 1, the developing roller 10 is provided with a metal core 12, a roller body 14 of electroconductive rubber, rolled around the core 12, and a coating layer 16 covering the outer circumferential surface of the roller body 14.

The core 12 may comprise any metal material as long as it has a predetermined rigidity and sufficient conductivity. In this embodiment, the core 12 is made of iron material. The roller body 14 has a size for forming an image on an A4 (210*297 mm) sized sheet, and it is φ6 mm in outer diameter. Further, in this embodiment, the roller body 14 is made of electroconductive silicone rubber. On the other hand, the coating layer 16 comprises electroconductive fluororesin coating material, and has an about 10 mm thickness.

The developing roller 10 has roller resistance within a range from 10 Ω to 10 Ω.

[Correlation between Glossiness Unevenness of Developing Roller 10 and Image Density Unevenness]

The quality of the developing roller 10 having the above construction depends on existence/absence of image density unevenness in case of image testing by forming a solid-black image on a sheet by an image forming apparatus using the developing roller 10. The inventor of the present application has performed a number of and various types of evaluation tests on the developing roller 10 and has found a predetermined correlation between the glossiness unevenness of the outer circumferential surface of the developing roller 10 and the image density unevenness. That is, the less the glossiness unevenness of the outer circumferential surface of the developing roller 10 becomes, the less the image density unevenness becomes. Hereinbelow, the correlation will be examined.

[Examination Method]

Twenty developing rollers 10, manufactured on the same condition, are measured on the conditions for glossiness measurement defined by JIS Z8741. The measured developing rollers 10 are sequentially installed in an image forming apparatus (laser-beam printer). The image forming apparatus is operated to sequentially output solid-black images, by using the developing rollers 10. Thereafter, the correlation between the density unevenness of the outputted images and the unevenness of the measured glossiness is evaluated.

[Measurement of Glossiness of Developing Roller 10]

First, the conditions for glossiness measurement will be described. In this measurement, a glossimeter VGS-1001DP manufactured by Nippon Denshoku Kogyo Co., Ltd. is used to measure specular glossiness at 75°, based on the JIS Z8741 glossiness measurement method 2 (example 1). Next, specular glossiness at 60° is measured by using this glossimeter, based on the JIS Z8741 glossiness measurement method 3 (example 2). Finally, specular glossiness at 45° is measured by using this glossimeter, based on the JIS Z8741 glossiness measurement method 4 (example 3).

The results of the example 1 are as shown in table 1; the results of the example 2 are as shown in table 2; and the results of the example 3 are as shown in table 3.

In the examples 1 to 3, each measurement has been performed at the central position regarding an axial direction of each developing roller 10. Further, each developing roller 10 is divided into four parts in its circumferential direction. Each measurement start position is denoted with "A". In tables 1 to 3, the glossiness measured at this position A is given in column A. When the measurement at the position A has been completed, the developing roller 10 is rotated by 90° in a clockwise direction, then the position where the developing roller 10 has stopped is denoted with "B". In tables 1 to 3, the glossiness measured at this position B is given in column B.

When the measurement at the position B has been completed, the developing roller 10 is rotated by 90° in the clockwise direction, then the position where the developing roller 10 has stopped is denoted with "C". In tables 1 to 3, the glossiness measured at this position C is given in column C. When the measurement, at the position C has been completed, the developing roller 10 is rotated by 90° in the clockwise direction, then the position where the developing roller 10 has stopped is denoted with "D". In tables 1 to 3, the glossiness measured at this position D is given in column D.

That is, the measurement values regarding one developing roller 10 are obtained at four positions A, B, C and D shifted by 90° at the central portion in the axial direction of the outer circumferential surface of the roller.

[Evaluation]

Regarding each developing roller 10, the logarithms (in this embodiment, common logarithms) of the respective maximum and minimum values of the four measurement values are taken, and the difference between these maximum and minimum logarithm values is obtained ($\Delta \log GS = \log GS_{max} - \log GS_{min}$), and written in column $\Delta \log Gs$ in tables 1 to 3. As it is clearly understood from these tables, regarding the $\Delta \log GS$ values less than "0.1", the image density unevenness of images outputted by using the corresponding developing rollers 10 are all determined by visual judgment as "good" (o), while regarding the $\Delta \log GS$ values equal to or greater than "0.1", the image density unevenness values of images outputted by using the corresponding developing rollers 10 are determined by visual judgment as "no good" (X).

Further, in these tables 1 to 3, the 75° specular glossiness values, the 60° specular glossiness values and the 45° specular glossiness values show tendencies similar to the above tendency. Accordingly, it is understood that the similar tendency is obtained, to whatever incident angle the glossimeter is set. This is very significant when applied to the testing method for the developing roller of the present invention. That is, regarding an incident angle in the glossimeter, if a predetermined correlation (dependency) exists between measured glossiness and image density unevenness, the incident angle must be precisely defined. However, since it is apparent from tables 1 to 3 that there is no correlation (dependency) between the measured glossiness and the image density unevenness, the incident angle of the glossimeter can be freely set, which easily performs testing operation, and is very convenient.

Note that regarding each developing roller 10, the difference between the maximum and minimum values of the four measurement values ($\Delta GS = \Delta S_{max} - \Delta S_{min}$) is obtained and the difference values are written in column $\Delta GS$ in tables 1 to 3, for reference. As it is apparent from these tables 1 to 3, there is no correlation between the $\Delta GS$ values and judgment of image density unevenness.

[Measurement of Surface Roughness of Developing Roller 10]

Conventionally, evaluation of the developing roller 10 has been made by measuring the surface roughness of the roller without actually outputting an image. Accordingly, as an example of comparison, measurement of the surface roughness is performed on twenty developing rollers 10 used in the above-described glossiness measurement, at the same measurement positions, and the correlation between the measured surface roughness and image density unevenness is examined.

First, the surface roughness test will be described. The surface roughness of the developing roller 10 are measured in the respective axial and circumferential directions, based on the old JIS standard. The measurement of surface roughness in the axial direction is made as a comparison example 1; and the measurement of surface roughness in the circumferential direction, as a comparison example 2. For surface roughness measurement, a surface-roughness measuring instrument Surfcom 570A manufactured by Tokyo Seimitsu Co., Ltd. is employed in the measurement in the axial direction of the developing roller 10, and in the measurement in the circumferential direction of the developing roller 10, a Surfcom 550A by the same company is employed. Similar to the above-described glossiness measurement, the surface roughness is measured at the above four positions, as central-line average roughness (Ra), maximum height (Rmax) and ten-point average roughness (Rz), based on the old JIS standard.

Note that as the conditions for measurement, in both axial and circumferential directions, the measurement length is 2.5 mm, the moving speed of the testing needle is 0.3 mm/sec, and the cut-off value upon Ra measurement is 0.8 mm.

The results of the comparison example 1 are as shown in table 4. Further, the results of the comparison example 2 are as shown in table 5.

Upon determination of correlation between the results of surface roughness measurement and the image density unevenness, calculation processing similar to the processing performed on the glossiness measurement values is performed on the surface roughness measurement values, for examination of the relation between the correlation and the above-described glossiness unevenness. That is, regarding each developing roller 10, the common logarithms of the maximum and minimum values of the four surface roughness measurement values are taken, and the difference between these common logarithm values is obtained (ΔlogR=logRmax−logRmin), and this value is written in column ΔlogR in tables 4 and 5. As it is clearly understood from these tables 4 and 5, there is no correlation between the ΔlogR values and the image density unevenness.

[Testing Method and Apparatus for Developing Roller 10]

Next, description will be made on testing method and apparatus which judges the developing roller 10 as "good"/"no good" in non-contact status, i.e., without actually installing the developing roller 10 in the image forming apparatus and test-running the apparatus to output a test image, by utilizing the correlation between the glossiness unevenness of the developing roller 10 and the image density unevenness, found by the inventor of the present application.

Figure 2:
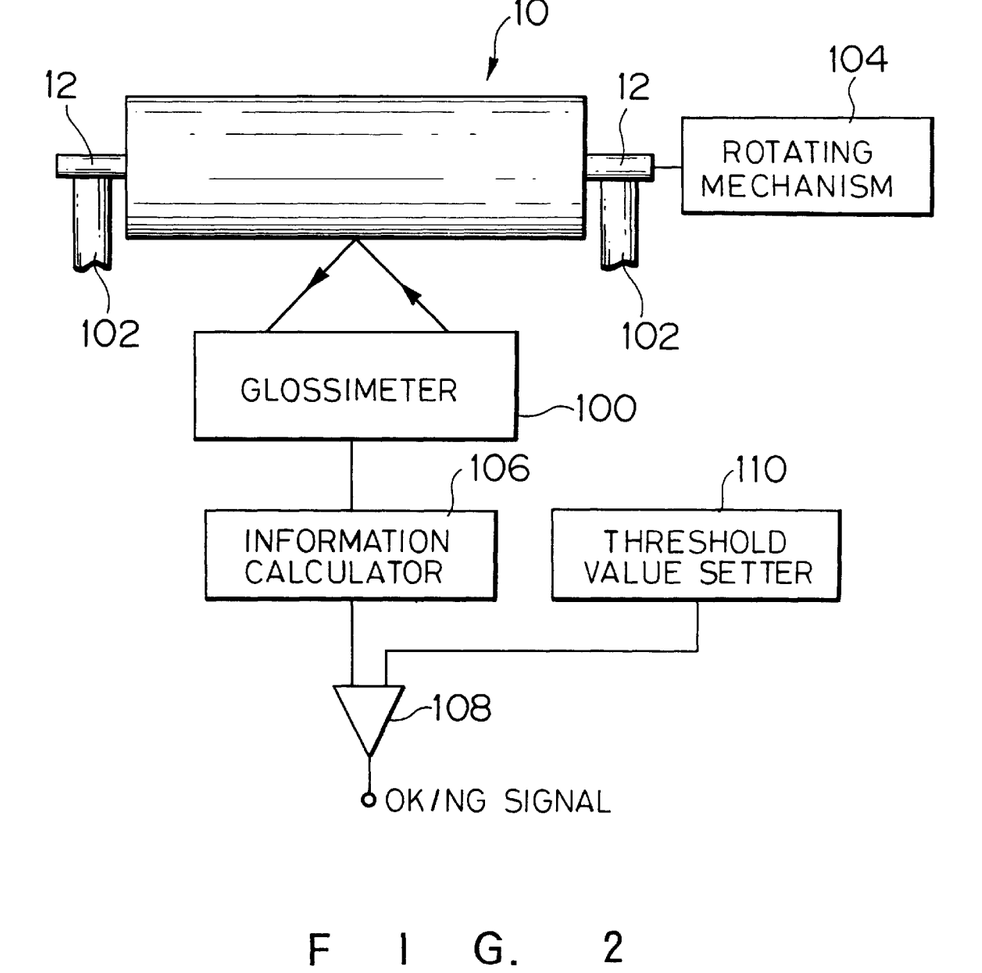
FIG. 2 is a block diagram showing a construction of a testing device in which the developing roller is to be tested.

In the testing method and apparatus, first, a developing roller 10, which has been newly manufactured, is placed on a platen 102 of a glossimeter 100 via a pickup mechanism (not shown), as shown in FIG. 2. In this status, the developing roller 10 is rotatably supported at its both ends of the core 12, and the developing roller 10 can be freely rotated on its central axis. Note that one end of the core 12 is connected to a rotation mechanism 104 for rotate-driving the developing roller 10 via a coupling member (not shown).

In the glossimeter 100, an incident angle with respect to the developing roller 10 is set such that detection light is emitted on a position lower than the central position in the axial direction of the developing roller 10 placed on the platen 102. As described above, as it is apparent that there is no correlation (dependency) between the incident angle and the image density unevenness, the incident angle can be freely set, which facilitates setting the testing apparatus.

On the other hand, when the developing roller 10 has been placed on the glossimeter 100, the testing light is emitted from the glossimeter 100 toward the position lower than the central position on the outer circumferential surface of the developing roller 10, in response to depression of a start key (not shown) by a tester (otherwise, when a sensor (not shown) detects that the developing roller 10 has been placed). At the same time, the rotation mechanism 104 is activated to rotate-drive the developing roller 10 to make only one revolution (rotate by 360°). Thus, the glossimeter outputs measured glossiness information.

The information output terminal of the glossimeter 100 is connected to an information calculator 106 which calculates the common logarithms of the maximum and minimum values of the measured glossiness information, and obtains the difference between these common logarithms (ΔlogGS), then outputs the result of calculation.

The output terminal of the information calculator 106 is connected to one input terminal of a comparator 108. The other terminal of the comparator 108 is connected to a threshold value setting unit 110 in which its threshold value is set to "0.1".

The comparator 108 compares the threshold value "0.1" outputted from the threshold value setting unit 110 with the ΔlogGS value outputted from the information calculator 106. If it determines that the ΔlogGS value is less than "0.1", the comparator 108 outputs an OK signal, while if it determines that the ΔlogGS value is equal to or greater than "0.1", the comparator 108 outputs an NG signal.

If the comparator 108 outputs the OK signal, the developing roller 10 is temporarily stored in a good-product container via the pickup mechanism (not shown) or directly conveyed to a station, where the developing roller 10 is installed into the image forming apparatus. On the other hand, if the comparator 108 outputs the NG signal, the developing roller 10 is put into a no good-product container via the pickup mechanism (not shown).

[Modifications]

The present invention is not limited to the above-described construction and procedure of the embodiment but various modifications can be made without departing from the scope of the invention.

For example, in the above-described embodiment, the common logarithms are taken to obtain the logarithm of glossiness information, however, this does not pose any limitation on the present invention; for example, similar tendency can be obtained by calculating the natural logarithm with the base "e". Note that in this case of obtaining the natural logarithm, the threshold value is varied in correspondence with the Logarithm.

Further, in the above-described embodiment, the information calculator 106 obtains the maximum value (Gsmax) and the minimum value (Gsmin) from the glossiness information, then, calculates the common logarithms of these maximum and minimum values (logGSmax, logGSmin), and obtains the difference between these common logarithms (ΔlogGS), however, the present invention is not limited on this procedure. It may be arranged such that the difference between the maximum and minimum values (MAx−MIN) is obtained with respect to the 75° 60° and 45° specular glossiness measurement values of the developing roller 10, then, the average value of the four values (AVG) is obtained, the ratio of the difference (MAX−MIN) with respect to the average value (AVG) by percentage (%) is obtained, and the percentage (%) value is used as a reference for "good"/"no good" determination.

The percentage (%) values for the 75° specular glossiness are as shown in table 6; the percentage (%) values for the 60° specular glossiness are as shown in table 7; and the percentage (%) values for the 45° specular glossiness are as shown in table 8.

As it is clearly understood from these tables 6 to 8, all the density unevenness values of images outputted by using the developing rollers 10 with the glossiness percentage (%) values less than 20% are determined as "good" (O) by visual judgment, while all the unevenness values of images outputted by using the developing rollers 10 with the glossiness percentage (%) values equal to or greater than 20%, are determined as "no good" (X) by visual judgment.

In this manner, the information calculator 106 not only calculates common logarithms or natural logarithms but also calculates percentages. In use of percentages, the calculation results can be used for judging the developing roller 10 as "good"/"no good" with 20% as the threshold value.

Note that the calculation to obtain a percentage is not limited to use of the average value (AVG) of the measurement information as the denominator. It is known that similar tendency is obtained from calculation using the maximum value (MAX) and the minimum value (MIN) of the measurement information. Although a table showing the results of calculation using the maximum and minimum values will be omitted to avoid overlapped description, it is apparent that any of these values can be used as the denominator of the percentage calculation for "good"/"no good" determination on the developing roller 10 with 20% as the threshold value.

Further, in the above-described embodiment, upon performing the testing method on the developing roller 10, the glossiness is measured at the central position of the developing roller along the axial direction, however, the present invention is not limited to this procedure. The measurement may be performed at an arbitrary position such as an end of the developing roller, in the axial direction along the circumferential direction.

Further, in the above-described embodiment, the measurement is performer while the relative position between the glossimeter 100 and the developing roller 10 is not changed, however, the present invention is not limited to this procedure. It may be arranged such that at least one of the glossimeter 100 and the developing roller 10 is moved along the central axis of the developing roller 10 while the developing roller is rotated, such that the relative position between them changes along the central axis of the developing roller 10. Thus, the spiral measurement on the outer circumferential surface of the developing roller 10 improves the reliability of the measurement.

In this case, the developing roller 10 may make only one revolution while the measurement at the relative position between the developing roller 10 and the glossimeter 100 covers the total length of the developing roller 10, otherwise, the developing roller 10 may make a plural number of revolutions.

Further, in the above-described embodiment, the measurement is continuously performed on the outer circumferential surface of the developing roller 10 in the circumferential direction, however, the present invention is not limited to this procedure. Even if interval measurement is performed at only the four points by 90°, the initial purpose of the measurement can be attained. That is, the measurement can be performed in continuous or interval manner as long as it is performed in a state where the outer circumferential surface of the developing roller 10 is divided into two or more parts.

Figure 3:
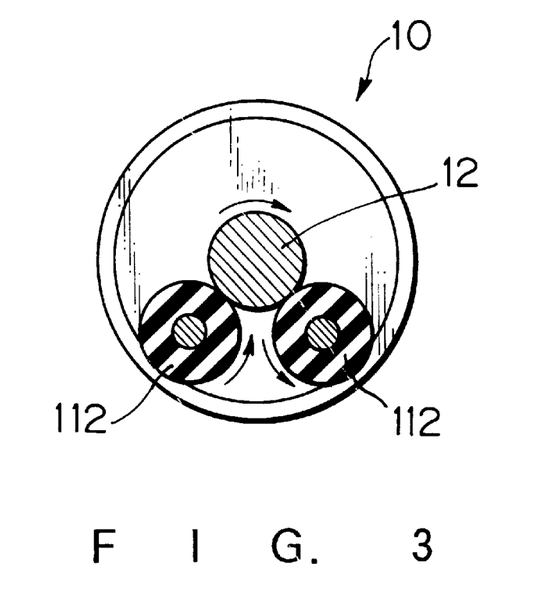
FIG. 3 is a side view showing a construction of a testing device in which a driving mechanism for rotating the developing roller is modified.

Further, in the above-described embodiment, the developing roller 10 is rotated by holding one end of the core 12 via the coupling member (not shown) and activating the rotation mechanism 104, however, the present invention is not limited to this arrangement. For example, as shown in FIG. 3 as a modification, both ends of the core 12 are placed on a pair of rollers 112 which rotate in the same direction, and these rollers 112 are rotate-driven in the same directions to rotate the developing roller 10 on its central axis. In this case, the developing roller 10 can be rotated by rotating only one of the rollers 112.

Further, in the above-described embodiment, the testing method is applied to the developing roller for the image forming apparatus, however, the present invention is not limited to this purpose, but can be applied to other process equipments such as a charging roller and a transfer roller, used in the image forming apparatus.

As the present invention may be embodied in several forms without departing from the spirit of essential characteristics thereof, the present embodiment is therefore illustrative and not restrictive, since the scope of the present invention is defined by the appended claims rather than by the description preceding them, and all changes that fall within meets and bounds of the claims, or equivalence of such meets and bounds are therefore intended to embraced by the claims.

TABLE 1

| Roller No. | Glossiness 75° | | | | | | Image Impression (Image Density Unevenness) |
|---|---|---|---|---|---|---|---|
| | A | B | C | D | ΔGS | ΔLogGS | |
| 1 | 6.4 | 6.3 | 6.4 | 6.0 | 0.4 | 0.028 | O |
| 2 | 6.9 | 7.3 | 7.0 | 6.1 | 1.2 | 0.078 | O |
| 3 | 5.2 | 5.4 | 5.4 | 5.4 | 0.2 | 0.016 | O |
| 4 | 6.1 | 6.1 | 6.5 | 6.4 | 0.4 | 0.028 | O |
| 5 | 5.6 | 6.1 | 6.5 | 6.1 | 0.9 | 0.065 | O |
| 6 | 5.3 | 5.4 | 5.6 | 5.7 | 0.4 | 0.032 | O |
| 7 | 4.8 | 4.7 | 5.0 | 5.1 | 0.4 | 0.035 | O |
| 8 | 6.0 | 6.1 | 5.7 | 5.6 | 0.5 | 0.037 | O |
| 9 | 6.1 | 6.3 | 6.3 | 6.0 | 0.3 | 0.021 | O |
| 10 | 5.2 | 5.0 | 5.2 | 5.3 | 0.3 | 0.025 | O |
| 11 | 6.0 | 4.5 | 4. | 5.6 | 1.9 | 0.165 | X |
| 12 | 7.8 | 6.2 | 4.9 | 6.2 | 2.9 | 0.202 | X |
| 13 | 7.7 | 5.4 | 4.2 | 5.0 | 3.5 | 0.263 | X |
| 14 | 7.1 | 5.1 | 4.2 | 5.7 | 2.9 | 0.228 | X |
| 15 | 7.5 | 6.1 | 4.1 | 4.5 | 3.4 | 0.262 | X |
| 16 | 7.9 | 5.2 | 3.9 | 5.5 | 4.0 | 0.307 | X |
| 17 | 7.1 | 4.9 | 4.0 | 5.4 | 3.1 | 0.249 | X |
| 18 | 4.5 | 3.4 | 2.8 | 3.5 | 1.7 | 0.206 | X |
| 19 | 7.2 | 4.9 | 4.3 | 5.8 | 2.9 | 0.224 | X |
| 20 | 6.7 | 4.7 | 3.9 | 4.9 | 2.8 | 0.235 | X |

TABLE 2

| Roller No. | Glossiness 60° | | | | ΔGS | ΔLogGS | Image Impression (Image Density Unevenness) |
|---|---|---|---|---|---|---|---|
| | A | B | C | D | | | |
| 1 | 1.8 | 1.8 | 1.9 | 1.9 | 0.1 | 0.023 | ○ |
| 2 | 1.8 | 2.1 | 2.1 | 2.0 | 0.3 | 0.067 | ○ |
| 3 | 1.5 | 1.6 | 1.6 | 1.6 | 0.1 | 0.028 | ○ |
| 4 | 1.8 | 1.7 | 1.7 | 1.7 | 0.1 | 0.025 | ○ |
| 5 | 1.8 | 1.5 | 1.7 | 1.6 | 0.3 | 0.079 | ○ |
| 6 | 1.7 | 1.8 | 1.7 | 1.7 | 0.1 | 0.025 | ○ |
| 7 | 1.5 | 1.4 | 1.5 | 1.5 | 0.1 | 0.030 | ○ |
| 8 | 1.7 | 1.7 | 1.8 | 1.7 | 0.1 | 0.025 | ○ |
| 9 | 1.8 | 1.8 | 1.8 | 1.9 | 0.1 | 0.023 | ○ |
| 10 | 2.0 | 1.9 | 1.8 | 1.9 | 0.2 | 0.046 | ○ |
| 11 | 1.7 | 1.8 | 1.3 | 1.3 | 0.5 | 0.141 | X |
| 12 | 2.4 | 2.0 | 1.5 | 1.7 | 0.9 | 0.204 | X |
| 13 | 2.6 | 1.9 | 1.2 | 1.6 | 1.4 | 0.336 | X |
| 14 | 2.2 | 1.6 | 1.2 | 1.7 | 1.0 | 0.263 | X |
| 15 | 2.0 | 1.8 | 1.2 | 1.2 | 0.8 | 0.222 | X |
| 16 | 2.6 | 1.7 | 1.2 | 1.6 | 1.4 | 0.336 | X |
| 17 | 2.3 | 1.9 | 1.3 | 1.4 | 2.0 | 0.248 | X |
| 18 | 1.6 | 1.2 | 1.0 | 1.2 | 0.6 | 0.204 | X |
| 19 | 2.4 | 1.7 | 1.3 | 1.9 | 1.1 | 0.266 | X |
| 20 | 2.0 | 1.9 | 1.2 | 1.2 | 0.8 | 0.222 | X |

TABLE 3

| Roller No. | Glossiness 45° | | | | ΔGS | ΔLogGS | Image Impression (Image Density Unevenness) |
|---|---|---|---|---|---|---|---|
| | A | B | C | D | | | |
| 1 | 1.0 | 1.0 | 1.0 | 1.0 | 0.0 | 0.000 | ○ |
| 2 | 1.0 | 1.0 | 1.0 | 1.0 | 0.0 | 0.000 | ○ |
| 3 | 0.8 | 0.8 | 0.8 | 0.8 | 0.0 | 0.000 | ○ |
| 4 | 0.9 | 0.9 | 0.9 | 0.9 | 0.0 | 0.000 | ○ |
| 5 | 1.0 | 0.9 | 1.0 | 0.9 | 0.1 | 0.046 | ○ |
| 6 | 1.0 | 1.0 | 1.0 | 0.9 | 0.1 | 0.046 | ○ |
| 7 | 0.9 | 0.8 | 0.8 | 0.8 | 0.1 | 0.051 | ○ |
| 8 | 0.9 | 0.9 | 1.0 | 0.9 | 0.1 | 0.046 | ○ |
| 9 | 1.2 | 1.1 | 1.1 | 1.0 | 0.2 | 0.079 | ○ |
| 10 | 0.9 | 0.9 | 0.9 | 0.9 | 0.0 | 0.000 | ○ |
| 11 | 0.9 | 0.9 | 0.7 | 0.7 | 0.2 | 0.1.9 | X |
| 12 | 1.2 | 1.1 | 0.9 | 0.9 | 0.3 | 0.125 | X |
| 13 | 1.2 | 1.0 | 0.7 | 0.8 | 0.5 | 0.234 | X |
| 14 | 1.1 | 0.9 | 0.7 | 0.9 | 0.4 | 0.196 | X |
| 15 | 1.0 | 1.0 | 0.7 | 0.7 | 0.3 | 0.155 | X |
| 16 | 1.4 | 1.1 | 0.8 | 1.0 | 0.6 | 0.243 | X |
| 17 | 1.2 | 1.1 | 0.8 | 0.8 | 0.4 | 0.176 | X |
| 18 | 1.0 | 0.8 | 0.7 | 0.7 | 0.3 | 0.155 | X |
| 19 | 1.2 | 1.0 | 0.7 | 1.0 | 0.5 | 0.234 | X |
| 20 | 1.0 | 1.1 | 0.7 | 0.8 | 0.4 | 0.196 | X |

TABLE 4

| Roller No. | Surface Roughness in Axial Direction (μm) | | | | | | | | | | | | | | | Image Impression (Image Density Unevenness) |
|---|---|---|---|---|---|---|---|---|---|---|---|---|---|---|---|---|
| | Ra | | | | | Rmax | | | | | Rz | | | | | |
| | A | B | C | D | ΔLogR | A | B | C | D | ΔLogR | A | B | C | D | ΔLogR | |
| 1 | 0.55 | 0.58 | 0.78 | 0.75 | 0.152 | 4.28 | 5.24 | 6.64 | 6.36 | 0.191 | 3.34 | 4.02 | 4.82 | 4.31 | 0.159 | ○ |
| 2 | 0.65 | 0.96 | 0.61 | 0.70 | 0.197 | 5.88 | 6.56 | 4.96 | 5.96 | 0.121 | 3.84 | — | 3.62 | — | — | ○ |
| 3 | 0.68 | 0.84 | 0.54 | 0.76 | 0.192 | 7.28 | 6.96 | 5.04 | 6.04 | 0.160 | 3.86 | 5.24 | 2.91 | 4.21 | 0.255 | ○ |
| 4 | 0.58 | 0.54 | 0.65 | 0.50 | 0.114 | 7.40 | 6.00 | 6.68 | 4.32 | 0.234 | — | — | — | 3.41 | — | ○ |
| 5 | 0.95 | 0.80 | 0.85 | 0.67 | 0.152 | 6.60 | 6.67 | 7.32 | 7.12 | 0.045 | 5.53 | 5.05 | 4.94 | — | — | ○ |
| 6 | 0.60 | 0.92 | 0.74 | 0.96 | 0.204 | 5.28 | 7.36 | 6.67 | 7.76 | 0.167 | 3.66 | 5.45 | 4.26 | 5.42 | 0.173 | ○ |
| 7 | 0.86 | 0.87 | 1.01 | 0.75 | 0.129 | 7.08 | 7.80 | 9.00 | 5.56 | 0.209 | 4.34 | 5.18 | — | 4.94 | — | ○ |
| 8 | 0.54 | 0.93 | 0.90 | 0.80 | 0.236 | 4.00 | 6.80 | 7.12 | 8.52 | 0.328 | 3.35 | 4.38 | 4.93 | 4.43 | 0.168 | ○ |
| 9 | 0.71 | 0.84 | 0.97 | 0.64 | 0.181 | 6.44 | 7.04 | 7.28 | 6.52 | 0.053 | 3.65 | 5.06 | 5.18 | 3.84 | 0.152 | ○ |
| 10 | 0.76 | 0.75 | 0.68 | 0.62 | 0.088 | 6.40 | 6.24 | 6.32 | 5.00 | 0.107 | 4.06 | 4.75 | 4.63 | 4.54 | 0.068 | ○ |
| 11 | 0.67 | 0.89 | 0.85 | 0.82 | 0.123 | 6.20 | 5.52 | 7.04 | 7.68 | 0.143 | 3.69 | 4.26 | 4.40 | 4.39 | 0.076 | X |
| 12 | 0.54 | 0.66 | 0.74 | 1.02 | 0.276 | 6.16 | 5.32 | 6.72 | 7.44 | 0.146 | — | 3.56 | 3.70 | 4.83 | — | X |
| 13 | 0.31 | 1.01 | 0.89 | 0.88 | 0.513 | 3.48 | 6.80 | 6.96 | 6.44 | 0.301 | 2.00 | 4.65 | 4.54 | — | — | X |

TABLE 4-continued

| Roller No. | Surface Roughness in Axial Direction (μm) | | | | | | | | | | | | | | | Image Impression (Image Density Unevenness) |
|---|---|---|---|---|---|---|---|---|---|---|---|---|---|---|---|---|
| | Ra | | | | | Rmax | | | | | Rz | | | | | |
| | A | B | C | D | ΔLogR | A | B | C | D | ΔLogR | A | B | C | D | ΔLogR | |
| 14 | 0.44 | 0.93 | 0.84 | 0.77 | 0.325 | 3.80 | 7.08 | 7.40 | 6.84 | 0.289 | — | 4.58 | 4.59 | — | — | X |
| 15 | 0.31 | 0.90 | 0.85 | 0.81 | 0.463 | 2.92 | 8.00 | 7.16 | 6.24 | 0.438 | 2.34 | — | 4.58 | 4.52 | — | X |
| 16 | 0.43 | 0.70 | 1.02 | 0.74 | 0.375 | 3.88 | 6.68 | 8.39 | 6.84 | 0.335 | 2.62 | — | 5.39 | 3.56 | — | X |
| 17 | 0.58 | 0.64 | 0.74 | 0.63 | 0.106 | 4.64 | 6.80 | 6.16 | 5.36 | 0.166 | 3.74 | — | 4.54 | 3.71 | — | X |
| 18 | 0.63 | 0.87 | 1.18 | 0.78 | 0.273 | 4.60 | 7.56 | 9.28 | 7.88 | 0.305 | 3.70 | 4.82 | 6.20 | 4.84 | 0.224 | X |
| 19 | 0.65 | 0.70 | 0.62 | 0.65 | 0.053 | 5.08 | 7.08 | 7.20 | 5.68 | 0.151 | 3.65 | — | — | 3.73 | — | X |
| 20 | 0.83 | 0.95 | 0.82 | 0.72 | 0.120 | 6.88 | 8.56 | 8.48 | 6.16 | 0.143 | 4.26 | — | 4.98 | 3.78 | — | X |

TABLE 5

| Roller No. | Surface Roughness in Circumferential Direction (μm) | | | | | | | | | | | | | | | Image Impression (Image Density Unevenness) |
|---|---|---|---|---|---|---|---|---|---|---|---|---|---|---|---|---|
| | Ra | | | | | Rmax | | | | | Rz | | | | | |
| | A | B | C | D | ΔLogR | A | B | C | D | ΔLogR | A | B | C | D | ΔLogR | |
| 1 | 0.72 | 0.95 | 1.11 | 0.87 | 0.188 | 5.80 | 8.10 | 8.30 | 7.25 | 0.156 | 4.58 | 5.76 | 6.24 | 5.23 | 0.134 | ○ |
| 2 | 1.02 | 0.85 | 0.86 | 0.64 | 0.202 | 7.55 | 5.90 | 6.00 | 6.30 | 0.107 | 5.97 | 4.93 | 4.67 | 4.49 | 0.124 | ○ |
| 3 | 0.64 | 1.07 | 0.80 | 0.96 | 0.223 | 5.00 | 8.88 | 6.10 | 7.90 | 0.249 | 4.34 | 6.04 | 4.65 | 5.25 | 1.144 | ○ |
| 4 | 0.97 | 0.74 | 1.00 | 0.78 | 0.131 | 8.60 | 5.05 | 13.50 | 6.70 | 0.427 | 5.95 | 3.99 | 7.23 | 5.90 | 0.258 | ○ |
| 5 | 1.26 | 0.95 | 1.15 | 0.78 | 0.208 | 10.15 | 6.75 | 8.95 | 6.90 | 0.177 | 7.15 | 5.78 | 6.07 | 5.19 | 0.139 | ○ |
| 6 | 1.04 | 1.25 | 1.15 | 1.24 | 0.080 | 7.30 | 8.95 | 9.05 | 10.85 | 0.172 | 5.86 | 7.05 | 6.00 | 6.88 | 0.080 | ○ |
| 7 | 1.05 | 1.04 | 0.97 | 1.22 | 0.100 | 7.25 | 9.80 | 8.65 | 8.15 | 0.131 | 6.09 | 7.01 | 5.87 | 6.50 | 0.077 | ○ |
| 8 | 1.04 | 0.83 | 0.64 | 0.86 | 0.211 | 7.70 | 8.20 | 4.95 | 6.05 | 0.219 | 5.96 | 7.80 | 3.98 | 4.84 | 0.292 | ○ |
| 9 | 0.96 | 0.99 | 1.10 | 0.79 | 0.144 | 5.90 | 7.40 | 7.50 | 6.90 | 0.1.4 | 5.17 | 5.60 | 6.29 | 5.15 | 0.087 | ○ |
| 10 | 0.97 | 1.11 | 1.13 | 0.99 | 0.066 | 9.45 | 8.15 | 7.25 | 6.50 | 0.163 | 5.65 | 6.75 | 6.15 | 5.57 | 0.083 | ○ |
| 11 | 0.79 | 0.84 | 1.11 | 1.13 | 0.220 | 7.05 | 7.50 | 7.65 | 7.90 | 0.049 | 4.72 | 4.95 | 6.04 | 7.22 | 0.185 | X |
| 12 | 0.58 | 0.78 | 1.13 | 0.89 | 0.290 | 5.50 | 7.80 | 8.20 | 7.55 | 0.173 | 3.80 | 5.13 | 5.85 | 5.20 | 0.187 | X |
| 13 | 0.62 | 1.22 | 0.89 | 0.95 | 0.294 | 5.90 | 9.00 | 7.05 | 9.85 | 0.223 | 4.15 | 6.81 | 5.57 | 6.34 | 0.215 | X |
| 14 | 0.64 | 0.93 | 1.15 | 0.84 | 0.255 | 6.50 | 7.55 | 8.15 | 6.35 | 0.108 | 3.52 | 5.38 | 6.06 | 4.90 | 0.236 | X |
| 15 | 0.69 | 0.91 | 1.04 | 1.16 | 0.226 | 6.05 | 6.55 | 7.25 | 7.65 | 0.102 | 4.64 | 5.17 | 5.93 | 6.42 | 0.141 | X |
| 16 | 0.70 | 1.20 | 1.68 | 1.18 | 0.380 | 7.30 | 8.55 | 11.45 | 8.00 | 0.195 | 4.38 | 6.79 | 8.50 | 6.18 | 0.288 | X |
| 17 | 0.93 | 1.14 | 1.25 | 1.08 | 0.128 | 6.35 | 8.15 | 9.70 | 7.30 | 0.184 | 4.89 | 5.80 | 7.73 | 6.13 | 0.199 | X |
| 18 | 1.04 | 1.29 | 1.52 | 0.89 | 0.232 | 7.60 | 8.85 | 13.55 | 6.80 | 0.299 | 5.57 | 7.13 | 8.07 | 5.91 | 0.161 | X |
| 19 | 0.66 | 0.99 | 1.19 | 1.14 | 0.256 | 6.65 | 6.80 | 9.45 | 9.65 | 0.153 | 4.44 | 5.74 | 7.20 | 6.68 | 0.210 | X |
| 20 | 0.88 | 0.89 | 1.19 | 1.10 | 0.131 | 6.70 | 7.50 | 8.75 | 6.65 | 0.119 | 5.11 | 5.23 | 6.64 | 5.23 | 0.113 | X |

TABLE 6

| Roller No. | 75° | | | | | | | | | |
|---|---|---|---|---|---|---|---|---|---|---|
| | A | B | C | D | MAX | MIN | MAX–MIN | AVG | % | Evaluation |
| 1 | 6.4 | 6.3 | 6.4 | 6.0 | 6.4 | 6.0 | 0.4 | 6.275 | 6.4 | ○ |
| 2 | 6.9 | 7.3 | 7.0 | 6.1 | 7.3 | 6.1 | 1.2 | 6.825 | 17.6 | ○ |
| 3 | 5.2 | 5.4 | 5.4 | 5.4 | 5.4 | 5.2 | 0.2 | 5.350 | 3.7 | ○ |
| 4 | 6.1 | 6.1 | 6.5 | 6.4 | 6.5 | 6.1 | 0.4 | 6.275 | 6.4 | ○ |
| 5 | 5.6 | 6.1 | 6.5 | 6.1 | 6.5 | 5.6 | 0.9 | 6.075 | 14.8 | ○ |
| 6 | 5.3 | 5.4 | 5.6 | 5.7 | 5.7 | 5.3 | 0.4 | 5.500 | 7.3 | ○ |
| 7 | 4.8 | 4.7 | 5.0 | 5.1 | 5.1 | 4.7 | 0.4 | 4.900 | 8.2 | ○ |
| 8 | 6.0 | 6.1 | 5.7 | 5.6 | 6.1 | 5.6 | 0.5 | 5.820 | 8.5 | ○ |
| 9 | 6.1 | 6.3 | 6.3 | 6.0 | 6.3 | 6.0 | 0.3 | 6.175 | 4.9 | ○ |
| 10 | 5.2 | 5.0 | 5.2 | 5.3 | 5.3 | 5.0 | 0.3 | 5.175 | 5.8 | ○ |
| 11 | 6.0 | 4.5 | 4.1 | 5.6 | 6.0 | 4.1 | 1.9 | 5.050 | 37.6 | X |
| 12 | 7.8 | 6.2 | 4.9 | 6.2 | 7.8 | 4.9 | 2.9 | 6.275 | 46.2 | X |
| 13 | 7.7 | 5.4 | 4.2 | 5.0 | 7.7 | 4.2 | 3.5 | 5.575 | 62.8 | X |
| 14 | 71 | 5.1 | 4.2 | 5.7 | 7.1 | 4.2 | 2.9 | 5.525 | 52.5 | X |
| 15 | 7.5 | 6.1 | 4.1 | 4.5 | 7.5 | 4.1 | 3.4 | 5.550 | 61.3 | X |

TABLE 6-continued

| Roller | 75° | | | | | | | | | |
|---|---|---|---|---|---|---|---|---|---|---|
| No. | A | B | C | D | MAX | MIN | MAX–MIN | AVG | % | Evaluation |
| 16 | 7.9 | 5.2 | 3.9 | 5.5 | 7.9 | 3.9 | 4.0 | 5.625 | 71.1 | X |
| 17 | 7.1 | 4.9 | 4.0 | 5.4 | 7.1 | 4.0 | 3.1 | 5.350 | 57.9 | X |
| 18 | 4.5 | 3.4 | 2.8 | 3.5 | 4.5 | 2.8 | 1.7 | 3.550 | 47.9 | X |
| 19 | 7.2 | 4.9 | 4.3 | 5.8 | 7.2 | 4.3 | 2.9 | 5.550 | 52.3 | X |
| 20 | 6.7 | 4.7 | 3.9 | 4.9 | 6.7 | 3.9 | 2.8 | 5.050 | 55.4 | X |

TABLE 7

| Roller | 60° | | | | | | | | | |
|---|---|---|---|---|---|---|---|---|---|---|
| No. | A | B | C | D | MAX | MIN | MAX–MIN | AVG | % | Evaluation |
| 1 | 1.8 | 1.8 | 1.9 | 1.9 | 1.9 | 1.8 | 0.1 | 1.850 | 5.4 | ○ |
| 2 | 1.8 | 2.1 | 2.1 | 2.0 | 2.1 | 1.8 | 1.3 | 2.000 | 15.0 | ○ |
| 3 | 1.5 | 1.6 | 1.6 | 1.6 | 1.6 | 1.5 | 0.1 | 1.575 | 6.3 | ○ |
| 4 | 1.8 | 1.7 | 1.7 | 1.7 | 1.8 | 1.7 | 0.1 | 1.725 | 5.8 | ○ |
| 5 | 1.8 | 1.5 | 1.7 | 1.6 | 1.8 | 1.5 | 0.3 | 1.650 | 18.2 | ○ |
| 6 | 1.7 | 1.8 | 1.7 | 1.7 | 1.8 | 1.7 | 0.1 | 1.725 | 5.8 | ○ |
| 7 | 1.5 | 1.4 | 1.5 | 1.5 | 1.5 | 1.4 | 0.1 | 1.475 | 6.8 | ○ |
| 8 | 1.7 | 1.7 | 1.8 | 1.7 | 1.8 | 1.7 | 0.1 | 1.725 | 5.8 | ○ |
| 9 | 1.8 | 1.8 | 1.8 | 1.9 | 1.9 | 1.8 | 0.1 | 1.825 | 5.5 | ○ |
| 10 | 2.0 | 1.9 | 1.8 | 1.9 | 2.0 | 1.8 | 0.2 | 1.900 | 10.5 | ○ |
| 11 | 1.7 | 1.8 | 1.3 | 1.3 | 1.8 | 1.3 | 0.5 | 1.525 | 32.8 | X |
| 12 | 2.4 | 2.0 | 1.5 | 1.7 | 2.4 | 1.5 | 0.9 | 1.900 | 47.4 | X |
| 13 | 2.6 | 1.9 | 1.2 | 1.6 | 2.6 | 1.2 | 1.4 | 1.825 | 76.7 | X |
| 14 | 2.2 | 1.6 | 1.2 | 1.7 | 2.2 | 1.2 | 1.0 | 1.675 | 59.7 | X |
| 15 | 2.0 | 1.8 | 1.2 | 1.2 | 2.0 | 1.2 | 0.8 | 1.550 | 51.6 | X |
| 16 | 2.6 | 1.7 | 1.2 | 1.6 | 2.6 | 1.2 | 1.4 | 1.775 | 78.9 | X |
| 17 | 2.3 | 1.9 | 1.3 | 1.4 | 2.3 | 1.3 | 1.0 | 1.725 | 58.0 | X |
| 18 | 1.6 | 1.2 | 1.0 | 1.2 | 1.6 | 1.0 | 0.6 | 1.250 | 48.0 | X |
| 19 | 2.4 | 1.7 | 1.3 | 1.9 | 2.4 | 1.3 | 1.1 | 1.825 | 60.3 | X |
| 20 | 2.0 | 1.9 | 1.2 | 1.2 | 2.0 | 1.2 | 0.8 | 1.575 | 50.8 | X |

TABLE 8

| Roller | 45° | | | | | | | | | |
|---|---|---|---|---|---|---|---|---|---|---|
| No. | A | B | C | D | MAX | MIN | MAX–MIN | AVG | % | Evaluation |
| 1 | 1.0 | 1.0 | 1.0 | 1.0 | 1.0 | 1.0 | 0.0 | 1.000 | 0.0 | ○ |
| 2 | 1.0 | 1.0 | 1.0 | 1.0 | 1.0 | 1.0 | 0.0 | 1.000 | 0.0 | ○ |
| 3 | 0.8 | 0.8 | 0.8 | 0.8 | 0.8 | 0.8 | 0.0 | 0.800 | 0.0 | ○ |
| 4 | 0.9 | 0.9 | 0.9 | 0.9 | 0.9 | 0.9 | 0.0 | 0.900 | 0.0 | ○ |
| 5 | 1.0 | 0.9 | 1.0 | 0.9 | 1.0 | 0.9 | 0.1 | 0.950 | 10.5 | ○ |
| 6 | 1.0 | 1.0 | 1.0 | 0.9 | 1.0 | 0.9 | 0.1 | 0.975 | 10.3 | ○ |
| 7 | 0.9 | 0.8 | 0.8 | 0.8 | 0.9 | 0.8 | 0.1 | 0.825 | 12.1 | ○ |
| 8 | 0.9 | 0.9 | 1.0 | 0.9 | 1.0 | 0.9 | 0.1 | 0.925 | 10.8 | ○ |
| 9 | 1.2 | 1.1 | 1.1 | 1.0 | 1.2 | 1.0 | 0.2 | 1.100 | 18.8 | ○ |
| 10 | 0.9 | 0.9 | 0.9 | 0.9 | 0.9 | 0.9 | 0.0 | 0.900 | 0.0 | ○ |
| 11 | 0.9 | 0.9 | 0.7 | 0.7 | 0.9 | 0.7 | 0.2 | 0.800 | 25.0 | X |
| 12 | 1.2 | 1.1 | 0.9 | 0.9 | 1.2 | 0.9 | 0.3 | 1.025 | 29.3 | X |
| 13 | 1.2 | 1.0 | 0.7 | 0.8 | 1.2 | 0.7 | 0.5 | 0.925 | 54.1 | X |
| 14 | 1.1 | 0.9 | 0.7 | 0.9 | 1.1 | 0.7 | 0.4 | 0.900 | 44.4 | X |
| 15 | 1.0 | 1.0 | 0.7 | 0.7 | 1.0 | 0.7 | 0.3 | 0.850 | 35.3 | X |
| 16 | 1.4 | 1.1 | 0.8 | 1.0 | 1.4 | 0.8 | 0.6 | 1.075 | 55.8 | X |
| 17 | 1.2 | 1.1 | 0.8 | 0.8 | 1.2 | 0.8 | 0.4 | 0.975 | 41.0 | X |
| 18 | 1.0 | 0.8 | 0.7 | 0.7 | 1.0 | 0.7 | 0.3 | 0.800 | 37.5 | X |
| 19 | 1.2 | 1.0 | 0.7 | 1.0 | 1.2 | 0.7 | 0.5 | 0.975 | 51.3 | X |
| 20 | 1.0 | 1.1 | 0.7 | 0.8 | 1.1 | 0.7 | 0.4 | 0.900 | 44.4 | X |

What is claimed is:

1. A method for testing an electroconductive roller which is to be installed in an image forming apparatus, comprising steps of:

a first step of setting a formed electroconductive roller at a position where a glossimeter can perform measurement on said electroconductive roller;

a second step of measuring glossiness of an outer circumferential surface of said electroconductive roller using said glossimeter;

a third step of performing a predetermined calculation on glossiness information of the outer circumferential surface of said electroconductive roller measured by said glossimeter; and a fourth step of comparing the result of said calculation with a predetermined threshold value and judging surface condition of said electroconductive roller.

2. The method according to claim 1, wherein at said second step, said electroconductive roller is rotated on its central axis, and wherein said glossiness is measured along at least a circumferential direction of the outer circumferential surface of said electroconductive roller using said glossimeter.

3. The method according to claim 2, wherein said glossiness is measured at two positions at least.

4. The method according to claim 2, wherein said glossiness is continuously measured.

5. The method according to claim 2, wherein at said second step, said glossiness is measured while a relative position between said electroconductive roller and said glossimeter is moved along the central axis of said electroconductive roller.

6. The method according to claim 1, wherein at said third step, calculation is performed to extract a maximum value and a minimum value of glossiness information measured by said glossimeter and obtain ac difference between logarithms of the maximum and minimum values.

7. The method according to claim 6, wherein at said fourth step, if the difference between the logarithms is less than the predetermined threshold value, it is judged that the surface condition of said electroconductive roller is good, while if the difference is equal to or greater than the predetermined threshold value, it is judged that the surface condition of said electroconductive roller is no good.

8. The method according to claim 1, wherein at said third step, calculation is performed to extract a maximum value and a minimum value of glossiness information measured by said glossimeter, obtain a difference between the maximum and minimum values, and obtain a ratio of the difference with respect to an average value of the glossiness information.

9. The method according to claim 8, wherein at said fourth step, if the ratio is less than the predetermined threshold value, it is judged that the surface condition of said electroconductive roller is good, while if the ratio is equal to or greater than the predetermined threshold value, it is judged that the surface condition of said electroconductive roller is no good.

10. The method according to claim 1, wherein said method is used for testing a developing roller in an image forming apparatus.

11. An apparatus for testing an electroconductive roller which is to be installed in an image forming apparatus, comprising:

placement means for placing a formed electroconductive roller, rotatably;

rotation means for rotate-driving said electroconductive roller placed on said placement means, on a central axis of said electroconductive roller;

measurement means for measuring glossiness of an outer circumferential surface of said electroconductive roller rotate-driven by said rotation means;

calculation means for performing a predetermined calculation on glossiness information obtained by said measurement means; and judgment means for comparing the result of the calculation with a predetermined threshold value and judging surface condition of said electroconductive roller.

12. The apparatus according to claim 11, further comprising:

moving means for moving a relative position between said electroconductive roller and said measurement means along an axial direction of said electroconductive roller by moving a position of measurement by said measurement means along the axial direction.

13. The apparatus according to claim 11, wherein said testing apparatus is used for testing a developing roller in an image forming apparatus.

* * * * *